United States Patent [19]

Francis

[11] 4,243,652

[45] Jan. 6, 1981

[54] GASTROINTESTINAL SCANNING AGENT

[75] Inventor: Marion D. Francis, Cincinnati, Ohio

[73] Assignee: The Procter & Gamble Company, Cincinnati, Ohio

[21] Appl. No.: 924,608

[22] Filed: Jul. 14, 1978

[51] Int. Cl.$^3$ .................. A61K 49/00; A61K 43/00; G01T 1/00

[52] U.S. Cl. .................................. 424/1; 128/653; 128/654; 128/659; 424/1.5; 424/9

[58] Field of Search .............. 424/1, 9; 128/653, 654, 128/659

[56] References Cited

U.S. PATENT DOCUMENTS

| | | | |
|---|---|---|---|
| 4,115,536 | 9/1978 | Rothman et al. | 424/1 |
| 4,115,540 | 9/1978 | Digenis et al. | 424/1 |

OTHER PUBLICATIONS

Chaudhuri et al., J. Nucl. Med., vol. 15, 1974, p. 483.
Mahmud et al., J. Nucl. Med., vol. 16, 1975, p. 547.
Heading et al., Gastroenterology, vol. 71, 1976, pp. 45-50.
Thomas et al., J. Nucl. Med., vol. 18, 1977, pp. 896-897.
Rezai-Zadeh et al., J. Nucl. Med., vol. 18, 1977, p. 635.
Theodorakis et al., J. Nucl. Med., vol. 16, 1975, p. 575.

*Primary Examiner*—Benjamin R. Padgett
*Assistant Examiner*—Christine M. Nucker
*Attorney, Agent, or Firm*—Steven J. Goldstein; Jerry J. Yetter; Richard C. Witte

[57] ABSTRACT

Technetium-99m has ideal characteristics for imaging the upper and lower GI tract and determining stomach emptying and intestinal transit time when used with an insoluble particulate material. For example, crystalline and amorphous calcium phosphate particles can be effectively labeled in a one-step process using $^{99m}TcO_4$ and $SnCl_2$. These labeled particles have insignificant mass and when administered orally pass through the GI tract unchanged, without affecting the handling and density of the intestinal contents. Visualization of the esophageal entry into the stomach, the greater and lesser curvatures of the stomach, ejection into the duodenum, and rates of passage through the upper and lower GI tract are obtained. The slurry of $^{99m}Tc$ particulate can be given rectally by enema. Good images of the cecum and the ascending, transverse, and descending colon are obtained. Mucosa folds and the splenic and hepatic flexures are visualized. The resilience of the large intestine is also readily visualized by pneumocolonographic techniques.

20 Claims, No Drawings

GASTROINTESTINAL SCANNING AGENT

TECHNICAL FIELD

Current methods for upper and lower gastrointestinal (GI) tract visualization rely primarily on the use of radiopaque contrast media. Although radiopaque contrast techniques yield good GI visualization and are widely used, they require an external source of X-rays. The high density contrast medium fills the GI tract and prevents the passage of the X-radiation through the soft tissue so that the organ being imaged is seen in contrast with the other, more radiolucent body tissues. When radiopaque media are used with X-rays to determine gastric emptying times or intestinal transit times, or to monitor the passage of material through the GI tract, the patient can be subjected to undesirable amounts of high energy radiation.

Moreover, the most common radiopaque agent used for GI imaging, barium sulfate, has several inherent disadvantages. The high density of this compound often results in intestinal impaction, thereby complicating disease states in which intestinal obstructions are already present. The dense barium compound moves slowly through the intestines so the time required to perform an upper or lower GI radiographic examination is lengthy, resulting in a greater exposure to radiation, especially when stomach emptying or intestinal transit times are being determined. Such determinations are often desired for pediatric patients, but prolonged exposure of children to radiation is particularly undesirable. Finally, administration of barium sulfate has resulted in intraperitoneal and extraperitoneal intestinal perforation and isolated cases of vascular invasion.

To avoid some of the problems associated with barium sulfate, water soluble reagents such as Hypaque$^{(R)}$ or Gastrograffin$^{(R)}$ have been developed as contrast media. These reagents take advantage of the high atomic weight of iodine and its high radiodensity. Both Hypaque and Gastrograffin are diatrizoates (tri-iodinated, substituted benzene compounds).

Unfortunately, some diatrizoates tend to be hyperosmotic and can cause a net diffusion of large volumes of water into the GI system, producing a water imbalance. This water imbalance can cause severe diarrhea and dehydration. For these reasons, these types of contrast media may be contraindicated for pediatric use since the child's body is unable to cope with the diarrhea and dehydration. As with barium sulfate, X-radiation must still be used with iodine-based radiopaque media.

Nonradiological techniques to determine gastrointestinal transit time have used inert compounds such as carbon black, ethylene oxide, and chromic oxide. The transit time is determined by the interval between the time of oral dose (actual dose of compound or mixture of compound with a test meal) to the time of appearance in the feces. Disappearance of polyethylene from gastric juice has been used as a measure of stomach emptying. These techniques avoid the radiation doses encountered when radiopaque media are used, but provide no visualization of the GI tract. When GI transit times or emptying times change, such nonradiological techniques do not help pinpoint the cause of the change.

It can be appreciated that the diagnosis of gastrointestinal conditions would be greatly aided by an effective GI visualization agent free from the foregoing problems.

The present invention provides an easily prepared radiolabeled composition of small particle size and physiologically insignificant mass which is easily distributed throughout the gastric contents, which can pass through the GI tract unchanged and without affecting the normal handling and density of the intestinal contents, and which can be monitored using standard scintigraphic techniques to measure or visualize the low intensity radiation of a gamma emitting radionuclide.

By the present invention, radionuclides such as $_{43}Tc^{99m}$, $_{49}In^{113m}$, and $_{49}In^{111}$ are used in combination with physiologically insoluble compounds to produce an effective and safe GI scanning agent.

BACKGROUND ART

Radiographic scanning agents suitable for use with gamma cameras, rectilinear scanners, and similar instruments have been prepared in different formulations for imaging of many human organs. Common radioisotopes used include 99m-technetium, 113m-indium, and 111-indium. These radionuclides are desirable for human use because they have low energy gamma radiation and short half lives.

Indium and technetium radioisotopes have been widely used in intravenous preparations for the radiographic imaging of body organs and systems. The following U.S. patents disclose typical radiographic compositions: U.S. Pat. No. 3,983,227, Tofe, diphosphonate dry mixture for admixture with technetium to produce bone scanning agent; U.S. Pat. No. 4,002,730, Hartman, technetium labelled anionic starch derivatives for lung imaging; U.S. Pat. No. 4,066,742, Garrett, technetium-sulfur colloid for imaging the reticuloendothelial system (RES); U.S. Pat. No. 4,070,493, Nadeau, stannous-phytate colloid for labeling with technetium to image the RES; U.S. Pat. No. 4,016,249, Adler, techentium-stannous pyrophosphate bone imaging agent; U.S. Pat. No. 4,017,595, Subramanian, indium-organic phosphonate bone imaging agent; U.S. Pat. No. 4,022,877, Shubert, technetium-organotin complexes for imaging the kidneys; U.S. Pat. No. 4,024,233, Winchell, technetium macroaggregated serum albumin compositions for lung imaging; U.S. Pat. No. 4,048,296, Wolfangel, technetium-sulfur colloid for imaging the RES; U.S. Pat. No. 4,057,616, Wolfangel, technetium labeled metal hydroxide colloids for lung imaging; U.S. Pat. No. 3,981,980, Baker, technetium labeled pyridoxals for imaging the biliary tract; and U.S. Pat. No. 3,992,513, Pethau, technetium labeled phospholipids for imaging the lung and liver.

Several literature articles refer to the use of 99m-technetium labeled diethylenetriaminepentaacetic acid (DTPA) for oral administration in determining gastric emptying times in humans and dogs. Chaudhuri, et al., J. Nucl. Med., 14, 622 (1973); Chaudhuri, J. Nucl. Med., 15, 391 (1974); and Chaudhuri, et al., J. Nucl. Med., 15, 483 (1974). The radiolabeled compound was added to a meal and was determined to be non-adsorbable and non-absorbable in the stomach and homogeneously distributed in the meal. Only gastric emptying times were investigated.

Further investigations into the determination of gastrointestinal physiological characteristics have involved technetium labeled sulfur colloids. Mahmud, et al., J. Nucl. Med., 16, 547, (1975) describe a method for evaluating and detecting gastroesophageal reflux. A 99m-technetium sulfur colloid was introduced to the stomach using a nasogastric tube. Heading, et al., Gastroenterology, 71, 45 (1976) disclose a double isotope scanning method for the simultaneous study of gastric emptying times of liquid and solid meal components. 113m-indium—DTPA was used as marker for the liquid phase and small pieces of paper impregnated with 99m technetium labeled sulfur colloid and encased in plexiglass were used to mark the solid phase. The double isotope method was adequate for determining gastric emptying times. Thomas, et al., J. Nucl. Med., 18, 896, (1977) disclose the use of a double isotope method to detect the afferent loop syndrome in the small intestine after failure to obtain adequate X-ray scans using barium. Intravenous iodine-131 labeled rose bengal was used to image the liver, and oral 99m-technetium labeled sulfur colloid was used as a solid phase marker for the double isotope measurement of gastric emptying. Rezai-Zadeh, et al., J. Nucl. Med., 18, 635 (1977) disclose the use of oatmeal and milk 99m-technetium sulfur colloid labeled meals to measure gastric emptying times in normal subjects.

Another technique reported in the literature for measuring gastric emptying times used a 99m-technetium labeled polyamine polymer formed from polystyrene and triethylenetetramine; Theodorakis, et al., J. Nucl. Med., 16, 575 (1975).

DISCLOSURE OF INVENTION

The present invention is based on the discovery that certain medically useful, gamma radiation emitting radionuclides can be employed in combination with particulate phosphate carriers to provide radiodiagnostic agents which are especially useful for scanning the GI tract, and the like.

As used, the radiodiagnostic agents of this invention comprise a gamma radiation emitting radionuclide in substantially permanent association with a pharmaceutically acceptable, substantially physiologically insoluble, particulate phosphate carrier of the type disclosed hereinafter.

The radionuclides which can be used herein include any of those gamma emitting radionuclides which are capable of becoming associated with substantially physiologically insoluble, particulate phosphate carrier materials; 99m-technetium, 113m-indium, and 111-indium are especially preferred for use herein. These radionuclides are thought to become substantially permanently associated with the particulate phosphate carriers employed herein, either by the formation of insoluble radionuclide oxides (e.g., technetium oxide) at the surface of the carrier, or by forming insoluble phosphate salts on the surface of the carrier, or, perhaps by exchanging with cations present in the phosphate carrier (e.g., exchange of the indium radionuclide cation for calcium cations in the preferred calcium hydroxylapatite carrier).

Whatever mechanism accounts for the association between the radionuclide and the phosphate carrier, it is important that the association be strong so that the radionuclide is not released to any significant extent from the carrier under the physiological conditions which obtain in the GI tract. If the radionuclide were to be released in soluble form from the carrier, either because of weak association or because the carrier, itself, were to be dissolved, the radionuclide would be free to be absorbed through the GI tract into the general circulatory system and surrounding soft tissues, thereby causing a blurred scan of the GI tract to be secured.

The present invention is notably easy to practice. As described more fully hereinafter, a solution of radionuclide such as the indium radionuclides mentioned hereinabove is simply mixed with the particulate phosphate carrier, whereupon the phosphate carrier becomes labeled with the radionuclide and is ready for use, either by oral administration or by enema.

The technetium radionuclide ($^{99m}$Tc) is most commonly available to hospitals in the form of a solution of pertechnetate ($^{99m}$TcO$_4^-$) wherein the technetium is in the +7 valence state. In order to be used in the practice of this invention, the pertechnetate must first be reduced to what is believed to be the +3, +4, or +5 valence state. This reduction of pertechnetate can be easily accomplished with well-known reducing agents such as various pharmaceutically-acceptable metal salts, especially stannous chloride.

The reduced $^{99m}$Tc in solution associates strongly and rapidly with the phosphate carrier particles on admixture. Accordingly, the present invention also encompasses reagents especially adapted for use in the preparation of technetium/phosphate carrier radiodiagnostic agents, said reagents comprising an amount of reducing agent sufficient to reduce the pertechnetate, and the aforesaid particulate phosphate carrier. Since many reducing agents are somewhat storage-unstable due to oxidation and/or hydrolysis, suitable stabilizing agents such as the gentisates, ascorbates, and the like, are preferably used in such reagents. In use, the reagent is simply admixed with the appropriate dose of radioactive pertechnetate solution (preferably aqueous), whereby the pertechnetate is reduced and essentially instantaneously labels the phosphate carrier. The resulting composition is administered orally or rectally to scan the GI tract.

Detailed means for practicing the invention are disclosed more fully hereinafter.

The pharmaceutically-acceptable, substantially physiologically insoluble, particulate phosphate carriers useful in the practice of this invention include the well-known compounds of the general M—P$_2$O$_5$—H$_2$O system, where M is a divalent cation, especially Ca (preferred), Mg, Ba and Sr. Such materials include the polyphosphates, apatites, and the like. Representative examples include: Ca$_3$(PO$_4$)$_2$; Ca$_4$H(PO$_4$)$_3$; Ca(H$_2$PO$_4$)$_2$ and its dihydrate; Ca$_2$P$_2$O$_7$; Ca$_4$P$_2$O$_9$; Ca$_8$H$_2$(PO$_4$)$_6$.5H$_2$O; CaHPO$_4$ and its insoluble hydrates; insoluble calcium polyphosphate; calcium hydroxylapatite, Ca$_{10}$(PO$_4$)$_6$(OH)$_2$; and the corresponding Mg, Ba and Sr phosphates.

The particulate phosphate carriers employed herein can be either amorphous or crystalline. The only lower limit to the size of the particles seems to be the unit cell dimensions of the carrier material. The upper limit depends on the comfort of the patient (grittiness). Typically, the particles have a size (avg. longest particle diameter) range of from about 10 Angstroms (Å) to about 5000 Å, more preferably from about 25 Å to about 2000 Å, most preferably from about 25 Å to about 500 Å.

By "pharmaceutically-acceptable" herein is meant that the phosphate carrier material can be administered to the patient without untoward physiological effects, consistent with an acceptable benefit/risk ratio attendant with any medical treatment.

By "substantially physiologically insoluble" herein is meant that the phosphate carrier does not substantially dissolve in the GI tract to release the radionuclide. It is unacceptable, from the standpoint of scan quality, for greater than about 10% of the radionuclide administered to be released in soluble form from the carrier into the GI tract; release of greater than about 2% is suboptimal. Any release of insoluble radionuclide from the carrier is inconsequential.

The amount of particulate phosphate carrier employed in the practice of the invention will depend to some extent on the size of the patient being treated. Overall, the usage range for human patients will be in the 50 mg. to 500 mg. range. For children and smaller animals the dose of phosphate carrier will usually be from about 50 mg. to about 100 mg.; for adults and comparably sized animals the dosage range will usually be from about 100 mg. to about 200 mg. For purposes of estimating dosage size, the usual amount of particulate phosphate carrier will range from about 1.5 mg./kg. (of body weight) to about 5 mg./kg.

The amount of radionuclide employed in the practice of this invention to provide good GI tract imaging can range from about 3 microCuries ($\mu$Ci)/kg. (of body weight) to about 300 $\mu$Ci/kg. The dosage of radionuclide will depend somewhat on the bulk of the human or lower animal patient and the type of GI scan being performed. For measuring gastrointestinal emptying times or gastroesophageal reflux, about 3 $\mu$Ci/kg. to about 40 $\mu$Ci/kg., preferably about 5 $\mu$Ci/kg. to about 15 $\mu$Ci/kg. are used. For measuring intestinal transit time with upper and lower GI visualization and visualization of abnormalities such as fistulas, blockages and herniations, radionuclide doses of about 10 $\mu$Ci/kg. to about 300 $\mu$Ci/kg., preferably about 30 $\mu$Ci/kg. to about 60 $\mu$Ci/kg. are used. For enema use, about 3 $\mu$Ci/kg. to about 40 $\mu$Ci/kg., preferably about 5 $\mu$Ci/kg. to about 15 $\mu$Ci/kg. are used. In any event, the amounts of particulate phosphate carrier specified hereinabove are more than ample to bind these dosages of radionuclide.

One mode of practicing the present invention employs pertechnetate and, as disclosed herein, a pertechnetate reducing agent. A great variety of pertechnetate reducing agents are known in the literature and such agents are suitable for use herein. Typical examples of such reducing agents include stannous chloride, chromous chloride, stannous sulfate, titanous chloride, ferrous chloride, ferrous sulfate, and the like. Compositions for hospital use will comprise an amount of pertechnetate reducing agent sufficient to reduce the pertechnetate-99m being used in the diagnostic procedure. Typically, an excess of reducing agent is employed since such small quantities of materials are involved. For example, compositions which contain from about 0.05 mg. to about 0.50 mg. of pertechnetate reducing agent are entirely adequate to reduce the typical dosage of pertechnetate.

When pertechnetate reducing agents are employed it is optimal to include an amount of stabilizer in the composition sufficient to prevent oxidation/hydrolysis of the pertechnetate reducing agent on storage. Such stabilizer materials include ascorbic acid, water-soluble ascorbate salts, gentisic acid, water-soluble gentisate salts, and like materials known in the radio-pharmaceutical arts. The amount of stabilizer employed in such compositions will depend to some extent on the amount of pertechnetate reducing agent present. In general, a weight ratio of stabilizer:reducing agent in the range from about 20:1 to about 1:1, preferably from about 5:1 to about 3:1, is ample. Typical compositions will contain from about 0.05 mg. to about 20 mg. of stabilizer.

The compositions of the present invention are administered in an amount effective to scan the GI tract, or the like. Administration can be orally by simply drinking or otherwise imbibing the radionuclide-labled phosphate carrier as an aqueous slurry. Slurries in orange juice, or mixtures in or with solid or semi-solid foods such as oatmeal or meat can also be used, as can catheterization. The compositions can also be administered rectally, by enema.

BEST MODE
STABILITY STUDY

The study was performed using a suspension formed with $SnCl_2$ (2 mg.), ascorbic acid (10 mg.) and hydroxyapatite (HA) (50 mg.; particle size range 25 Å to 100 Å). The components were combined in a scintillation vial; the $SnCl_2$ was added in an $N_2$ glove bag. 5.0 ml. of $^{99m}TcO_4^-$ saline solution was added, the mixture swirled and filtered. The clear filtrate was quantitatively transferred to a 50 ml. volumetric flask. Two distilled $H_2O$ washings from the filtering flask were also added, and the resultant volume diluted to 50 ml. with distilled $H_2O$. Two 15 ml. portions of 6N HCl were used to dissolve the solid. The solution was also drawn through the filter, collected, transferred to a 100 ml. volumetric flask, along with 2 distilled $H_2O$ washes, and diluted to 100 ml. with distilled $H_2O$. Upon completion of filtration, the 0.45 $\mu$m filter was removed and placed in a scintillation vial for $^{99m}Tc$ assay. The scintillation vial used for the original mixing of $^{99m}TcO_4^-$ and dry mix was also rinsed with two 3 ml. portions of 6N HCl, twice with 3 ml. portions of distilled $H_2O$, and the resultant solution transferred to a 25 ml. volumetric flask and diluted to 25 ml. with distilled $H_2O$. One ml. aliquots of solid (1:100 dil.), filtrate (1:50 dil.) and vial rinse (1:25 dil.), and the filter paper were assayed for $^{99m}Tc$ activity.

The distribution of radioactivity was calculated and was as follows: $^{99m}Tc$ activity was 98.3% labeled on the HA and 1.7% in filtrate.

ANIMAL STUDIES

I. A male dog was fasted 24 hours prior to rectal administration of a $^{99m}Tc$-HA suspension. The suspension to be administered was previously prepared by adding 10 ml. of $^{99m}TcO_4^-$ solution (3.3 mCi) to the dry contents as prepared in the foregoing section, and was warmed prior to dosing. Ten ml. of the $^{99m}Tc$-HA suspension was slowly introduced to the anesthetized dog followed by a 10 ml. saline wash of the dosing syringe and 150 ml. of normal saline solution in 50 ml. portions. After dosing, the dog was turned on its back and its limbs immobilized with the anterior portion of the dog elevated 20 degrees. Scintiscans were taken at 15, 18, and 20 minutes post-dose from the ventral view, inversion to the y axis, and counts preset to 200,000. Approximately one-half of the enema solution was then withdrawn. A single scintiscan was taken of the relatively "empty" colon, then scintiscans were taken after introduction of 50 and 100 ml. of air.

Results of scanning performed using rectal administration of the $^{99m}Tc$ dosing suspension are as follows. At 20 minutes visualization of the cecum, ascending colon, transverse colon and descending colon was obtained. Changes in distribution of suspension and diameter of the colon were seen before and after withdrawal of fluid and introduction of air. Blood samples drawn after initial filling of the colon and after final drainage indicated that $^{99m}$Tc activity in the total blood volume was only 0.012% and 0.05% of dose, respectively.

As with barium sulfate, a slurry of $^{99m}$Tc-HA can be given rectally by enema for lower bowel imaging. Good images of the cecum and the ascending, transverse and descending colon were obtained. Mucosal folds and the splenic and hepatic flexures were visualized. After partial drainage of the $^{99m}$Tc suspension, the resilience of the large intestine was readily visualized by filling the cavity with air and subsequent release of injected air.

II. A stable $^{99m}$Tc-HA suspension was prepared using 3 ml. $^{99m}$TcO$_4^-$ (2.2 mCi). The suspension of HA reaction mix was then drawn into a 3 ml. syringe attached to a rubber catheter. The catheter was inserted into the mouth, and thence into the stomach, of a male Sprague-Dawley rat (300 g.) which had been previously anesthetized with Nembutal, 30 mg./kg. (50 mg./ml.). After insertion, the suspension was injected into the stomach, and the catheter was removed and assayed for residual $^{99m}$Tc activity. The rat was placed on its back (ventral view) under the collimator of the gamma camera. Scintiscans were taken at 2, 4, 15, 30, 60 minutes and 11 hours post-dose.

Results of scans taken after oral dosing of $^{99m}$Tc-HA suspension to the anesthetized animal were as follows. The initial, 2 minute, scan showed the greatest $^{99m}$Tc activity in the stomach, clearly outlining the greater and lesser curvatures. The esophageal entry into the stomach showed some activity as did the duodenal exit from the stomach. Subsequent scans at 30 and 60 minutes post-dose indicated partial movement of the suspension further into the duodenum. At the time of the final scan, 11 hours, $^{99m}$Tc activity had decreased in the stomach. The activity appeared in the cecum, and transverse and ascending colon.

III. The dry components were mixed together as described in the foregoing sections using 100 mg. HA and 20 mg. ascorbic acid; the level of SnCl$_2$ remained 2 mg. The volume of the $^{99m}$TcO$_4^-$ added to the dry components was 10 ml. with an activity of 17.4 mCi. The suspension was swirled about 10 minutes and then drawn into a 10 ml. syringe connected to a rubber stomach tube. The rubber tube was inserted into the stomach of an unanesthetized male dog, and the entire 10 ml. of suspension volume introduced, followed by a 10 ml. saline rinse, to remove residual $^{99m}$Tc activity from the tube. Scintiscans were taken at 3, 5, 15, 30, 38, 41 and 60 minutes, and 2, 3, 4, 6, 9 and 24 hours post-dose with the animal positioned in right lateral recumbency, resulting in a left lateral camera view. Inversion was to the y axis with count level preset at 100,000 counts and unlimited preset time. Scintiscans were also taken of the thyroid and bladder regions to detect possible $^{99m}$Tc activity resulting from oxidation of the $^{99m}$Tc to $^{99m}$TcO$_4^-$. After the 9-hour scintiscan was complete, the animal was held overnight in a metabolism cage to facilitate feces and urine collections which were held until decay of $^{99m}$Tc. The 24-hour scintiscans were performed the following morning.

Results of scans obtained after oral administration of the $^{99m}$Tc-HA suspension to an unanesthetized dog were as follows. At the initial 3-minute scan the stomach was clearly visible with activity already moving into the upper duodenum. The suspension steadily evacuated from the stomach and proceeded further into the small intestine. By about 60 minutes post-dose, the majority of the activity had left the stomach. Throughout the following two scans at two and three hours, the passage of the suspension further through the various segments of the small intestine was evident. At 4 hours and 5 minutes, the ascending and transverse colon were outlined. By the final 6-hour scan the activity had traveled through the entire intestinal system and was seen leaving the transverse colon and concentrating in the descending colon.

Oral administration of the $^{99m}$Tc-HA suspension to both rat and dog resulted in visualization of the stomach and small and large intestines. The particulate labeled with $^{99m}$Tc initially distributed uniformly in the stomach and with time could be observed moving through the gastrointestinal tract, limited solely to that system. Times for stomach emptying and passage through various segments of the intestine could be determined. Stomach emptying was estimated at about 60 minutes in the unanesthetized dog with a longer emptying time in the anesthetized rat.

Examination of thyroid revealed no uptake, indicating a negligible (unvisualized) amount of $^{99m}$TcO$_4^-$ in the suspension. Similarly, scans of the bladder area revealed no indication of activity, suggesting little or no urinary handling (systemic load) of the $^{99m}$Tc-HA preparation. By contrast, when $^{99m}$TcO$_4^-$ solution is administered orally, there is high uptake in the stomach, bladder and thyroid, with a generalized soft tissue background activity.

CONVENIENT MODE

In a convenient mode, the present invention provides technetium-labeled GI scanning agents by using skeletal radiodiagnostic agents which are already commercially available to hospitals. The only requirement for adapting the commercially available skeletal radiodiagnostic agents for use in the practice of the present invention is that such radiodiagnostic agents must contain a reducing agent for pertechnetate. Such radiodiagnostic agents usually contain a calcium phosphate-type targeting agent such as an organic phosphonate or inorganic pyrophosphate, which is designed to preferentially target the technetium to specific sites of calcific activity in the body. The presence or absence of such targeting agents does not substantially interfere with the practice of the present invention, although somewhat sharper GI scans are secured when such targeting agents are not present.

As an example of this convenient mode, the $^{99m}$Tc-HA was prepared by adding 500 mg. of HA to a dry vial of commercial OSTEOSCAN (Procter & Gamble Company, Cincinnati, Ohio; mixture of SnCl$_2$, NaCl, ascorbate stabilizer and sodium salts of ethane-1-hydroxy-1,1-diphosphonic acid). The contents were then suspended in 5.0 ml. of $^{99m}$TcO$_4^-$ (16.0 mCi) in saline. After mixing, 1 ml. of suspension was withdrawn and diluted to 10 ml. with saline, resulting in an activity of ~2.6 mCi. The final concentration of HA was 100 mg./10 ml. The suspension was dosed orally to a male dog via a syringe connected to a rubber catheter, and was followed by a 10 ml. saline wash. The dog had been positioned in a sling for scintigraphy. Scanning commenced immediately upon initial injection of $^{99m}$Tc suspension, with the catheter still in place. Scintiphotos were taken at 0, 3, 15, 39, 48, and 60 minutes and 2, 3, 4½, 5, 6, and 6½ hours post-dose. Scintiscans were again taken of the thyroid and bladder regions to detect any $^{99m}$Tc activity in those areas. Following the 6½ hour scintiscan, the dog was housed overnight in a metabolism cage for collection of urine and feces. At 24 hours post-dose, final scintiscans were performed. Results were much the same as disclosed above, but some details of the scans were not as sharp as with the HA product without the diphosphonate present.

It will be appreciated that the foregoing procedures are useful in the same manner for GI imaging in human patients, with appropriate modifications with regard to size of dosage, as disclosed hereinabove. For human patients ranging in size from children to the average adult (70 kg.) the radiation dose will typically range from about 100 μCi to about 20,000 μCi per scan.

INDUSTRIAL APPLICABILITY

The compositions of the present invention are used to scan the GI tract, and to determine physiological characteristics and diagnose medical problems which occur in the GI tract. Several significant benefits are obtained.

(1) Such small quantities of solid composition are used that the composition does not influence or adversely affect the stomach or intestinal function.

(2) In contrast to fluoroscopic methods using radiopaque materials, dosimetry to the subject is not increased by the length or number of observations made on the subject when the present compositions are used.

(3) Apart from the radiation from the radionuclide which is dosage related and can be controlled at a safe level, none of the components of the present compositions are toxic to the patient.

(4) The present technique can be practiced using Indium-113m or Indium-111 in place of the preferred $^{99m}$Tc. $^{113m}$In, especially, has many properties similar to those of $^{99m}$Tc such as inexpensive production and a half-life which is suitably short for medical uses. As noted, in one significant respect $^{113m}$In is unlike $^{99m}$Tc. Indium is not absorbed by the GI tract as $^{99m}$Tc is when in the form of $^{99m}$TcO$_4^-$. Moreover, the indium radioisotopes react directly with the particulate phosphate carriers used herein, especially calcium hydroxylapatite. Thus, the indium radioisotopes do not require a reducing agent.

As can be seen from the foregoing, the present invention encompasses radiodiagnostic agents comprising: a gamma radiation emitting radionuclide (especially $^{99m}$Tc, $^{113m}$In or $^{111}$In) in substantially permanent association with a pharmaceutically-acceptable, substantially physiologically insoluble, particulate phosphate carrier. The particulate phosphate carrier is preferably a calcium phosphate compound, especially calcium hydroxylapatite. The most highly preferred radiodiagnostic compositions prepared according to this invention comprise: from about 100 μCi to about 5000 μCi of $^{99m}$technetium in substantially permanent association with from about 50 mg. to about 500 mg. of calcium hydroxylapatite particles having an average particle size of from about 25 Å to about 500 Å.

The invention also encompasses reagents for preparing $^{99m}$Tc-based radiodiagnostic agents for use in the GI tract, or the like, comprising: an effective amount of a pertechnetate reducing agent (especially pharmaceutically-acceptable, water-soluble stannous, ferrous, chromous and titanous salts, with stannous chloride being preferred) and an effective amount of a pharmaceutically-acceptable, substantially physiologically insoluble, particulate phosphate carrier, said reagent being in the form of a powder. Such reagents also preferably comprise a calcium phosphate compound as the particulate carrier, again, with calcium hydroxylapatite being preferred. Preferably, such reagents are dry powders, stored under dry nitrogen, and comprise from about 0.05 mg. to about 0.25 mg. of stannous chloride and from about 50 mg. to about 500 mg. of calcium hydroxylapatite particles having an average particle size of from about 25 Å to about 500 Å.

The invention also encompasses stabilized reagents for preparing a $^{99m}$Tc-based radiodiagnostic agent for use in the GI tract, or the like, comprising: an effective amount of a pertechnetate reducing agent (as above), an effective amount of a pharmaceutically-acceptable, substantially physiologically insoluble, particulate phosphate carrier (as above), and an effective amount of a stabilizer (preferably ascorbic acid or a water-soluble, pharmaceutically-acceptable salt thereof, especially sodium ascorbate, or gentisic acid or a water-soluble salt thereof, especially sodium gentisate). Preferred stabilized reagents of this type (which can optionally be stored under N$_2$) comprise from about 0.05 mg. to about 0.25 mg. of stannous chloride, from about 50 mg. to about 500 mg. of calcium hydroxylapatite particles having an average particle size (diameter) of from about 25 Å to about 500 Å and from about 0.25 mg. to about 1.0 mg. of a stabilizer selected from ascorbic acid, sodium ascorbate, gentisic acid and sodium gentisate.

The invention also encompasses a process for preparing a reagent suitable for use as a radiodiagnostic agent in the GI tract, or the like, comprising admixing from about 100 μCi to about 5000 μCi of a gamma radiation emitting nuclide (as above) with a pharmaceutically-acceptable, substantially physiologically insoluble, particulate phosphate carrier (as above) said mixing being carried out in aqueous solution, whereby said radionuclide is substantially permanently associated with said carrier. When the radionuclide is in the form of pertechnetate, it must be converted to a suitably reduced form, as disclosed above.

The invention also encompasses a process for visualizing the GI tract, comprising administering to a human or lower animal a radiodiagnostic agent comprising the gamma radiation emitting radionuclide in substantially permanent association with the pharmaceutically-acceptable, substantially physiologically insoluble, particulate phosphate carrier.

The following examples further illustrate the practice of this invention, but are not intended to be limiting thereof.

EXAMPLE I

Stannous chloride (0.16 mg.) and sodium ascorbate (0.50 mg.) are admixed with calcium hydroxylapatite (avg. diam. 100 Å; 150 mg.) and stored as a dry powder in a sealed vial under N$_2$.

The powder prepared in the foregoing manner is admixed with about 5 ml. (200 μCi) of a pertechnetate-99m solution from a commercial source. The pertechnetate is reduced and a stable GI scanning agent suitable for oral or rectal use is secured within about two minutes.

EXAMPLE II

A collecting vial containing 0.2 mg. of sodium gentisate, 0.16 mg. of stannous chloride and 500 mg. of calcium hydroxylapatite (particle diameter range 25 Å to 500 Å) is placed at the elute orifice of a pertechnetate- 99m generator. Seven mls. of saline eluate are collected in the vial. The sodium gentisate is dissolved, the pertechnetate is reduced, and the suspended apatite is labeled with ca. 2500 μCi of the reduced $^{99m}$Tc. The suspension is mixed with 15 mls. of orange juice and swallowed by a human patient. The esophagus and stomach are visualized with an Anger camera, using standard radiographic techniques.

EXAMPLE III

The compositions of Examples I and II are each modified by replacing the stannous chloride with an equivalent amount of the following reducing agents: stannous sulfate, chromous chloride, chromous sulfate, ferrous chloride, ferrous sulfate, titanous chloride, titanous bromide, and stannous fluoride, respectively. In each instance, good labeling of the apatite is achieved within a minute, or so, of mixing. The compositions are administered orally and rectally to visualize the upper and lower GI tract of humans and lower animals.

EXAMPLE IV

The compositions of Examples I, II and III are modified by replacing the calcium hydroxylapatite with an equivalent amount of the following insoluble metal apatites, respectively (average size range 10 Å to 5000 Å): strontium apatite, barium apatite, magnesium apatite, and stannous apatite. In each instance, GI scanning agents suitable for human or veterinary use are secured.

EXAMPLE V

The compositions of Examples I, II, III and IV are modified by replacing the apatites with an equivalent amount of the following pharmaceutically-acceptable, substantially physiologically insoluble, particulate phosphate carriers, respectively (average particle size range 25 Å to about 500 Å): $Ca_3(PO_4)_2$; $Ca_4H(PO_4)_3$; $Ca(H_2PO_4)_2$ and its dihydrate; $Ca_2P_2O_7$; $Ca_4P_2O_9$; $Ca_8H_2(PO_4)_6 \cdot 5H_2O$; $CaHPO_4$ and its insoluble hydrates; and insoluble calcium polyphosphate. In each instance, GI scanning agents suitable for human or veterinary use are secured.

EXAMPLE VI

Commercial calcium hydroxylapatite having an average particle size range of 25 Å to 500 Å is obtained. A unit dose of the powdered apatite (200 mg.) is admixed with a solution of 113m-indium chloride (3000 μCi). The suspension of apatite particles in the indium solution is swirled for about two minutes, admixed with cooked oatmeal, and ingested by a patient. Excellent GI scanning is secured. As can be seen from the foregoing, the present invention employs particulate carriers which can be conveniently obtained in the desired particle size range by standard synthetic methods. Uniform particles are readily secured without the problems associated in the manufacture of sulfur colloid-type GI scanning agents, and the like, where the control of colloid size can be difficult.

What is claimed is:

1. A radiodiagnostic agent, comprising:
   A. A gamma radiation emitting radionuclide in substantially permanent association with;
   B. A pharmaceutically-acceptable, substantially physiologically insoluble, particulate inorganic phosphate carrier.

2. The composition of claim 1 wherein said radionuclide is $^{99m}$technetium, $^{113m}$indium or $^{111}$indium.

3. The composition of claim 1 wherein said particulate phosphate carrier is a calcium phosphate compound.

4. A composition according to claim 3 wherein the calcium phosphate compound is calcium hydroxylapatite.

5. A composition according to claim 1, comprising:
   A. From about 100 μCi to about 5000 μCi of $^{99m}$technetium in substantially permanent association with;
   B. From about 50 mg. to about 500 mg. of calcium hydroxylapatite particles having an average particle size of from about 25 Å to about 500 Å.

6. A reagent for preparing a $^{99m}$Tc-based radio-diagnostic agent for use in the GI tract, or the like, comprising:
   A. An effective amount of a pertechnetate reducing agent; and
   B. An effective amount of a pharmaceutically-acceptable, substantially physiologically insoluble, particulate inorganic phosphate carrier;
said reagent being in the form of a powder.

7. A reagent according to claim 6 wherein the pertechnetate reducing agent is selected from pharmaceutically-acceptable, water-soluble stannous, ferrous, chromous and titanous salts.

8. A reagent according to claim 7 wherein the reducing agent is stannous chloride.

9. A reagent according to claim 6 wherein the particulate phosphate carrier is a calcium phosphate compound.

10. A reagent according to claim 9 wherein the calcium phosphate compound is calcium hydroxylapatite.

11. A reagent according to claim 6, comprising:
    A. From about 0.05 mg. to about 0.25 mg. of stannous chloride; and
    B. From about 50 mg. to about 500 mg. of calcium hydroxylapatite particles having an average particle size of from about 25 Å to about 500 Å.

12. A reagent for preparing a $^{99m}$Tc-based radio-diagnostic agent for use in the GI tract, or the like, comprising:
    A. An effective amount of a pertechnetate reducing agent; and
    B. An effective amount of a pharmaceutically-acceptable, substantially physiologically insoluble, particulate inorganic phosphate carrier; and
    C. An effective amount of a stabilizer.

13. A composition according to claim 12 wherein the pertechnetate reducing agent is selected from pharmaceutically-acceptable, water-soluble stannous, ferrous, chromous and titanous salts.

14. A composition according to claim 13 wherein the reducing agent is stannous chloride.

15. A composition according to claim 12 wherein the particulate phosphate carrier is a calcium phosphate compound.

16. A composition according to claim 15 wherein the calcium phosphate compound is calcium hydroxylapatite.

17. A composition according to claim 12 wherein the stabilizer is selected from ascorbic acid, or its water-soluble salts, or gentisic acid, or its water-soluble salts.

18. A reagent according to claim 12, comprising:
    A. From about 0.05 mg. to about 0.25 mg. of stannous chloride;
    B. From about 50 mg. to about 500 mg. of calcium hydroxylapatite particles having an average particle size of from about 25 Å to about 500 Å; and C. From about 0.25 mg. to about 1.0 mg. of a stabilizer selected from ascorbic acid, sodium ascorbate, gentisic acid and sodium gentisate.

19. A process for preparing a reagent suitable for use as a radiodiagnostic agent in the GI tract, or the like, comprising admixing from about 100 $\mu$Ci to about 20,000 $\mu$Ci of a gamma radiation emitting nuclide with a pharmaceutically-acceptable, substantially physiologically insoluble, particulate inorganic phosphate carrier, said mixing being carried out in solution, whereby said radionuclide is substantially permanently associated with said carrier.

20. A process for visualizing the GI tract of humans and lower animals, comprising introducing into the GI tract of a human or lower animal a radiodiagnostic agent comprising a gamma radiation emitting radionuclide in substantially permanent association with a pharmaceutically-acceptable, substantially physiologically insoluble, particulate inorganic phosphate carrier.

* * * * *